United States Patent [19]
Hernandez

[11] Patent Number: 4,581,237
[45] Date of Patent: Apr. 8, 1986

[54] CANNERY SPOILAGE AVOIDANCE METHOD

[76] Inventor: Richard Hernandez, 1625 Richland Ave., Ceres, Calif. 95307

[21] Appl. No.: 616,709
[22] Filed: Jun. 4, 1984
[51] Int. Cl.$^4$ ............................ C12Q 1/06; C12Q 3/00
[52] U.S. Cl. ........................................ 426/231; 435/34
[58] Field of Search ................... 426/231; 435/29, 31, 435/34, 39, 803; 422/79

[56] References Cited

U.S. PATENT DOCUMENTS 2,063,245 12/1936 Haeseler .............................. 426/231
4,385,113 5/1983 Chappelle et al. ..................... 435/34

Primary Examiner—George Yeung
Attorney, Agent, or Firm—Mark C. Jacobs

[57] ABSTRACT

An anti-spoilage technique for canners of syrup pack fruits is disclosed which technique requires a determination of the thermophile content in the well water used to supply the syrup room of a cannery, and a monitoring of a thermophile threshold level of such well water, whereby upon exceeding of the threshold level, the well water source can be shut down and a second well having a thermophile content below the threshold level in its water is used as the water source for the cannery syrup room. This technique can also be used by canners of water pack vegetables.

7 Claims, 3 Drawing Figures

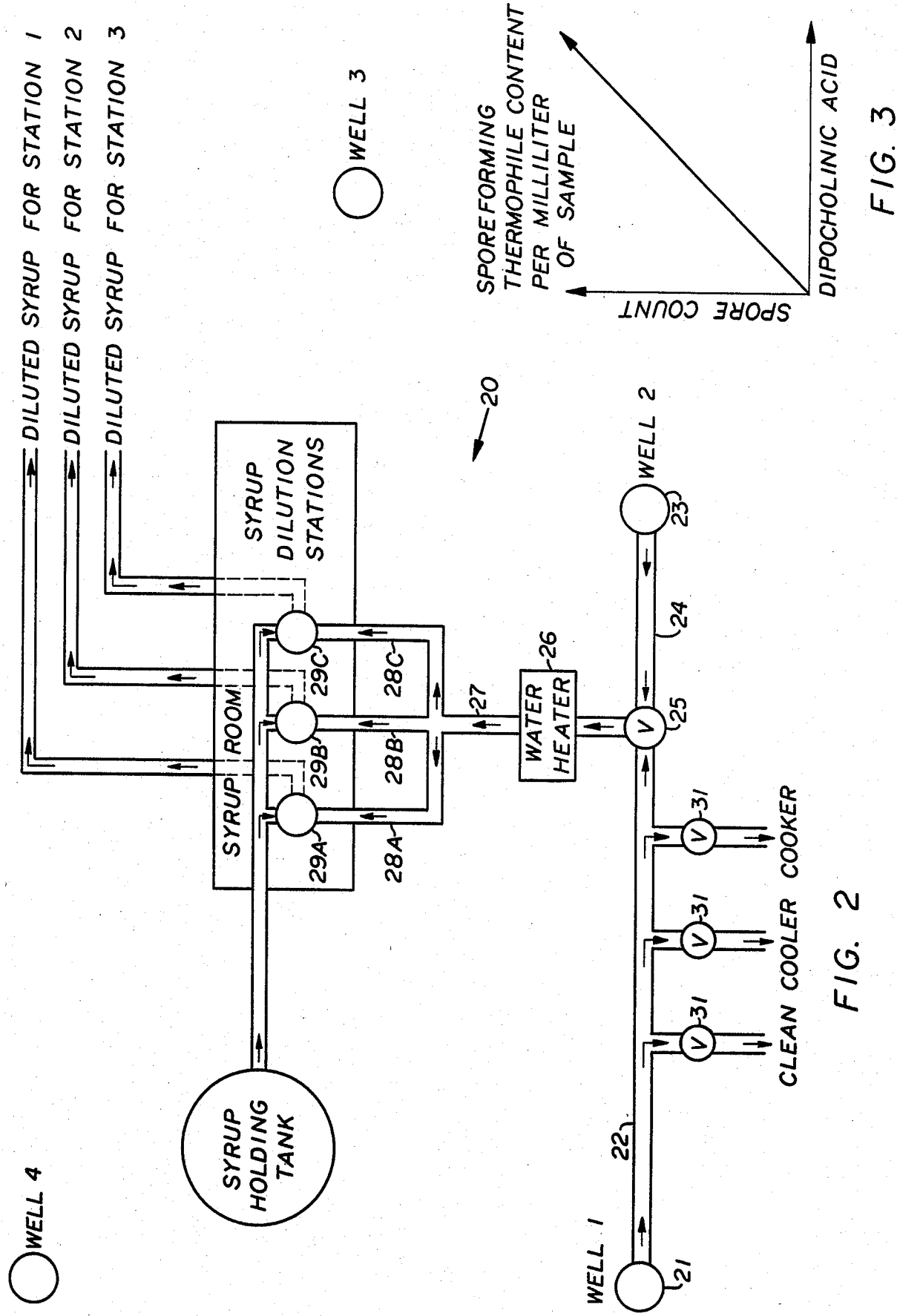

CANNERY SPOILAGE AVOIDANCE METHOD

BACKGROUND OF THE INVENTION

Thermophiles, as is known in the world of microbiology, are bacteria that grow in heated environments. That is, they thrive in conditions of 45 to 75 degrees centigrade and grow best within the range of 50–60 degrees centigrade. This translates to 122 to 140 degrees fahrenheit as the preferred range. Among thermophiles the most heat resistant are known as the "sporeforming thermophiles". Specifically the two most common are clostridium and bacillus. The effect thereof in the canning process will become evident from a reading of the material to follow.

Normally during a canning season in California, a cannery experiences only a few days of work wherein the products canned later turn spoiled. This few days of bad product can and did amount last year for one cooperative canner in a $350,000.00 loss. The loss or spoilage manifests itself to cans swelling up and in many instances actually exploding in the warehouses within three (3) to four (4) days after the canning process. Since canned goods are serialized, it is usually easy to isolate a batch that has or may be spoiled, and discard same. Unfortunately the spoilage determinations are always made after the fact. This results not only in lost fruit, but also lost production time, and lost cans as well.

One cannery known to the inventor hereof, which is located in Oregon, lost forty percent (40%) of its canned pears in a recent year to product spoilage. It is my contention that this spoilage arose, and the spoilage of product in other canneries arises, due to an excessive amount of sporeforming thermophiles in the syrup water.

All canneries are designed to employ several water sources, for the various tasks of the cannery. But, every cannery known to the inventor has but a single well source of water for the syrup dilution in the syrup room. Since syrup dilution (from 70–80% down to 8–12%) is one of the foremost aspects of canning, it is believed that human error can be avoided according to current cannery technology by utilizing only water from one well in the syrup room. I say well source, because the U.S.D.A. will not permit water that has been chlorinated to be used in the canning of food.

Several years ago the inventor of the instant technique set out to determine why the spoilage took place. I theorized that the problem might lie in the well water used in the syrup room, even though I knew that the canning process involved high heat, high enough to kill about 1000 thermophiles per milliliter of water-syrup mixture in any given canned fruit.

It is an object therefore of this invention to provide a process for avoiding canned fruit spoilage.

It is another object to provide a process for determining times likely in the canning period when spoilage will occur.

It is yet another object to provide a method to avoid canned fruit product spoilage once the likelihood thereof is ascertained.

A further object is to provide an improved cannery layout that will be able to avoid the canned fruit spoilage problem.

Other objects of the invention will in part be obvious and will in part appear hereinafter.

The invention accordingly comprises the method involving the several steps and the relation and order of one or more of such steps with respect to each of the others, and to the apparatus possessing the the construction, combination of elements and arrangement of parts which are exemplified in the following detailed disclosure and the scope of the application of which will be indicated in the appended claims.

For a fuller understanding of the nature and objects of the invention, reference should be had to the following detailed description taken in connection with the accompanying drawings.

SUMMARY OF THE INVENTION

An improved process for the syrup pack canning of fruit is disclosed which avoids spoilage of product, believed to be caused by high sporeforming thermophile content in the process water, by monitoring the sporeforming thermophile content of well water used in the syrup room, and alternating water sources should the sporeforming thermophile content exceed a safe threshold level.

BRIEF DESCRIPTION OF THE DRAWINGS

FIG. 2 is a diagrammatic layout of a cannery according to this invention.

FIG. 3 is a graphical plot of sporeforming thermophile count versus the amount of dipicolinic acid in a gas liquid chromatographic analysis of a well water sample.

DESCRIPTION OF THE PREFERRED EMBODIMENT

Figure 1:
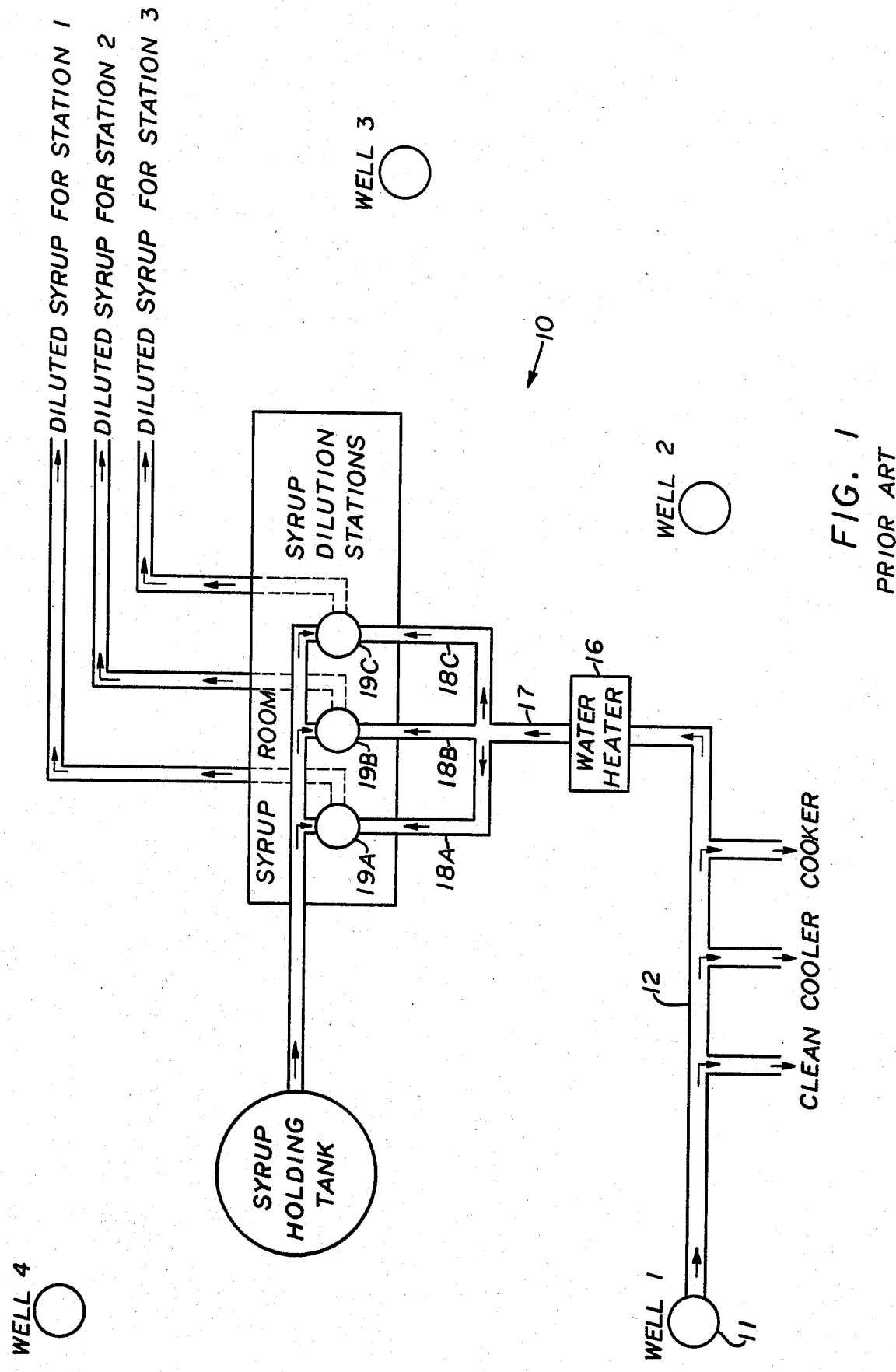
FIG. 1 is a diagrammatic layout of a portion of a typical cannery, which constitutes the prior art.

Being cognizant of the high spoilage experienced at a central valley of California packer in 1982, I decided to investigate to determine the cause of this spoilage. I knew that well water was used in the syrup room, and I also knew in the back of my mind that even if the water was later found to be the causative agent of the spoilage, that the substitution of distilled water for well water would be extremely expensive and not cost effective.

Many people had thought that the problem lay in contaminated cans but I was not so certain. I knew that all cans being processed go through the cookers and that the cookers can usually sterilize all of the bacteria. However, I also knew that if there are an excess of bacteria present that you can not kill them all. I was reviewing the canning process to determine what could be a source of bacteria that could cause spoilage.

I thought that perhaps the problem lay in the water. While I knew that in the past the syrup room's well water on occasion had contained large amounts of bacteria, I had never made a count of the bacteria nor had I correlated bacteria count to days of spoilage.

Why every cannery has only one well source for the syrup room I do not know. But it is a fact of the canning industry. I then decided to check out the water used in the syrup room. I found that there were two methods to determine the amount of sporeforming thermophiles in well water. The first method makes use of agar. It is an incubation technique. A sample is withdrawn from the well; the water is placed in the agar medium and the content in bacteria permitted to grow. A count is then taken. This technique is well known in the art. While a very inexpensive method, the mode suffers the major drawback of requiring a two day incubation period.

The second method utilizes gas chromotgraphy. The advantage here is that the determination only requires a two hour time period; while the drawback is the expense.

However, when one realizes that $100,000 of losses can easily arise in one day, it is seen that if the few days of spoilage that occur in any one season can be prevented, the instrument can pay for itself.

I then sent out to employ both methods of checking the water from the well that supplied the syrup room of a California central valley cannery. For a whole season I monitored the water, using both of the techniques recited above. The details of the monitoring procedures are recited in the specific examples.

I monitored the sporeforming thermophile content of the water from the well of the syrup room for the 1983 season. I was already aware of the fact that the canning process is adapted to kill off up to 1000 thermophiles per ml. of water in the can. Thus if from any one or more sources of possible invasion of sporeforming thermophiles, the content exceeded 1000/ml, I anticipated that spoilage would occur. This was based upon the analyses of previously spoiled cans for thermophile content.

The sources of sporeforming thermophile other than the syrup room well water include the environmental air, the cans utilized, the operators (even though they wear gloves). the syrup itself, the water based conveyor system utilized to transport cut pieces of fruit from station to station, and perhaps others. As to any and all of these potential sources of excessive amounts of thermophiles, none of these can be altered to inhibit or prevent them from promoting thermophile content growth. Thus to ensure a safety cushion beneath the 1000/ml count, since any one of these sources can easily get out of control due to negligence or unintentional activity thereby causing the total thermophile content to increase significantly, I have determined that a level of spore-forming thermophiles within the well water below about 400 will provide adequate safety margin should one of these other sources go excessive in order to stay below the 1000 count per ml. A formula can be set out as follows:

$$\text{syrup room well water S.F.T.C.} + \text{other sourfaces of S.F.T.C.} = X \text{ SFT/ml of canned fruit product}$$

wherein X=the number of sporeforming thermophile/ml the cookers are capable of killing in the processing and S.F.T.C. stands for sporeforming thermophile content.

Fortunately, I monitored not only the syrup room's well. but other wells utilized by the cannery. I discovered firstly that the number of high thermophile content days of any one well during a canning season was very few. I also discovered that the thermophile level of all of the wells being monitored was not the same every day. While well #1 might be extremely high, well #2 might be acceptable that day, and a few days later, the reverse condition could be true.

It then occurred to me to devise a system for shifting the source of water for the syrup room from whatever well was supplying the syrup room on the day previous to a high count day, e.g. well #1 to an alternate well, e.g. well #2. In light of the formula set forth above and having postulated this process. I then devised a system that employed a diverter valve for changing the source of supply to the syrup room. The implementation of this valve results in a new design for a syrup pack fruit cannery.

Reference is made to FIGS. 1 and 2 which represent the standard prior art cannery 10 and my improved cannery 20 respectively.

In the cannery of FIG. 1, the water from well #1 is piped through pipe 12 to water heater 16 wherein it is heated to the proper temperature prior to distribution through delivery tubes 18a,b, and c which deliver the process water to each of the syrup dilution stations 19a,b, and c.

In contrast my invention cannery 20 has water from well #1, 23 piped through pipe 22 to a two way valve 25. Water from well #2 is delivered through pipe 24 to the same valve 25. The water from either source takes the same path to the heater 26, then via pipe 27 to delivery tubes 28a,b, and c to each of the syrup dilution stations 29a, b, and c.

It is seen that any two way valve suitable for use in a cannery may be employed in my improved cannery. Many such valves are available in the marketplace.

While a trio of wells could be so interlinked and of course is contemplated, the number of above threshold days is so few in any one canning season, that for cost effectiveness, it is probably only necessary to link two to the syrup room.

While the drawings here depict a simple mechanical valve, an electronic controlled as well as mechanical valve of any type is contemplated.

It is further to be noted that in both FIGS. 1 and 2 well #1 is seen to service the syrup room and other needs of the cannery. Well 2 is dedicated solely to the syrup room. My invention contemplates either or both being multi-user or dedicated wells servicing only the syrup room.

Turning back momentarily to FIG. 2 it is also suggested that in order to stretch out the availability of good water (low thermophile content) that secondary valves 31 be installed at the various junctions along pipe 22 where other areas of the cannery are tied to the well #1 water source. This a recommended procedure but is not necessary to the invention.

The following specific Examples illustrate a non-limiting process of determining sporeforming thermophile content in water using an agar incubation method, and using gas chromatographic analysis.

EXAMPLE 1

Plate Count of Sporeforming Thermophiles

Plate counts are made to estimate the number of bacteria in water. To selectively estimate the number of sporeforming thermophiles it is first necessary to destroy all other bacteria. This is accomplished simply by heating the water to be tested to 80° C. for ten (10) minutes. Only sporeforming thermophiles will survive this heat test. The sporeforming thermophiles according to Holdeman, L. V., Cato, E. P., and Moore, W. E. C., editors; Anaerobe Laboratory Manual. ed. 4, Blacksburg, VA., 1977, Virginia Polytechnic Institute and State University, can now be counted with plate count agar.

Materials:
Freshly collected well water in a sterile 500 ml flask.
Plate count agar
Bunsen burner
Celsius thermometer
Disposable 1 ml pipette Petri dishes
Procedure:
1. Collect about 200 ml of well water in a sterilized 500 ml flask.
2. Use a bunsen burner to bring up the temperature of the well water to 80° C. for ten (10) minutes. Begin timing only after the water temperature has reached 80° C. Continuously check the temperature with a celcius thermometer.
3. With a disposable sterile pipette, transfer 1 ml of heated water to a petri dish. Label date and well source.
4. The sterilized plate count agar should be allowed to cool until it is warm then poured into petri dish containing the 1 ml of well water. Swirl gently in a circular manner for about one (1) minute. Allow it to sit until agar hardens.
5. Place the petri dish upside down in an incubator, set at 37° C. or forty-eight (48) hours. Count each colony of bacteria seen growing in the agar. Results should read thermophiles per ml of well water.

EXAMPLE 2

Sporeforming Thermophile Count by Gas-Liquid Chromotography

Bacterial spore from thermophiles contain dipicolinic acid. A correlation can be made between the amount of dipicolinic acid present in water and the sporeforming thermophile count. Making a standardized curve possible.
Materials:
Gas liquid chromatography instrument
1 li of freshly collected well water
Biological filter paper
Centrifuge
Trimethylphenylammonium hydroxide
Silver oxide
Methyl isobutyl ketone
Tetramethylammonium hydroxide
Lutidinic acid
Sulfuric acid
Dipicolinic acid
Ammonium sulfate
Bunsen burner
Procedure:
1. Collect one liter of well water. Bring the sample water temperature up to 80° C. for ten (10) minutes. Then follow agar method of determining sporeforming thermophiles.
2. Filter the liter of well water thru a biological filter which traps all bacteria.
3. Run a GLC analysis on the biological filter, for dipicolinic acid.
4. Make a standard curve; sporeforming thermophile agar count vs. amount of dipicolinic acid present.

It is known that agar counting can take up to several days to get a reading on the thermophile content, while the chromatographic analysis can be done in a few hours or so. While more costly, the latter is a real time procedure allowing for almost instant well switching.

As mentioned earlier herein, the major source of sporeforming thermophiles in a cannery is from the well water, which can be controlled by shifting from one well source to another, thus utilizing my process. Since most canneries are specifically designed to kill 1000 sporeforming thermophiles per ml of fluid in any given can, i.e., small 8 ounce cans are cooked ten (10) minutes and larger gallon cans are cooked for twenty-four (24) minutes. If the number of sporeforming thermophiles exceeds 1000 per ml of fluid in any given can, the cookers are not able to kill 100% of all the thermophiles and spoilage will occur. It is possible, however, that in any specific cannery that the safe threshold level will be over or under 400 thermophiles per ml of water. This threshold level can, of course, be determined by correlating spoilage days to the thermophile content of the well water used on the day of processing the spoiled product. However if the cannery cooker is designed to kill about 1000 sporeforming thermophiles per ml of fluid in a given can, the threshold should be about the same.

It is seen that I have devised an improved cannery design that employs my discovery that in most canneries a thermophile content of 400 or less in the syrup room well water will not cause spoilage in end product. The procedure thus requires the operator to first determine the killing power of the cooker; to then monitor the well water for thermophile content; and to determine a safe threshold of sporeforming thermophiles by correlating past spoilage to well water thermophile count to obtain a safe threshold level and to alternate water sources to the syrup room to stay below the threshold level.

While a single valve, valve system, that acts to alternate well sources is depicted in the drawings, obviously two individual on-off valves could be used as a valve system to accomplish the same result.

It is also beneficial to employ a small faucet at a convenient location in the water line from each well to make testing of the water convenient for the monitoring chemist.

Since certain changes may be made in the above apparatus and method without departing from the scope of the invention herein involved, it is intended that all matter contained in the above description and shown in the accompanying drawings shall be interpreted as illustrative and not in a limiting sense.

I claim:
1. In a method for reducing the sporeforming thermophile content in a syrup packed food, which is prepared in a cannery cooker and utilizes syrup from a syrup making room that employs water, in order to avoid spoilage of the packed food, the improvement comprising:
   a. determining the thermophile killing capacity of the cannery cooker,
   b. measuring the sporeforming thermophile content of the water from a first sources that supply the syrup making room,
   c. correlating the days of spoiled product occurrence to the sporeforming thermophile content of the syrup making room water to determine a threshold level of excessive sporeforming thermophiles,
   d. alternating the water from the first source to a second source on days that the content of the first source exceeds the safe threshold level of sporeforming thermophiles as determined by continued monitoring of the water from the first and second water sources, said second water source has a safe threshold level of sporeforming thermophiles.
2. In the process of claim 1 wherein the monitoring is done by agar counting of thermophiles.
3. In the process of claim 1 wherein the monitoring is done by gas chromatographic analysis of the water for dipicolinic acid.

4. In the process of claim 1 wherein the water source is changed from a first source to a second source when the threshold level of said first source is above 400 sporeforming thermophiles per ml.

5. In the process of claim 1 wherein the alternating of the water is carried out by a valve system.

6. In the process of claim 5 wherein the alternating step is performed by turning a multi port valve from a first to a second source of water to the syrup room, the number of ports of said valve being equal to the number of sources of water.

7. In the method of claim 1 wherein the first and second water sources are well water sources.

* * * * *